(12) United States Patent
Ding et al.

(10) Patent No.: US 10,589,276 B2
(45) Date of Patent: Mar. 17, 2020

(54) MULTI-FUNCTIONAL MICROFLUIDICS DEVICE FOR BIOLOGICAL SAMPLE SCREENING

(71) Applicant: Shenzhen Genorivision Technology Co., Ltd., Shenzhen (CN)

(72) Inventors: Rui Ding, Shenzhen (CN); Peiyan Cao, Shenzhen (CN)

(73) Assignee: SHENZHEN GENORIVISION TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 16/117,824

(22) Filed: Aug. 30, 2018

(65) Prior Publication Data

US 2018/0369819 A1    Dec. 27, 2018

Related U.S. Application Data

(63) Continuation of application No. PCT/CN2016/079128, filed on Apr. 13, 2016.

(51) Int. Cl.
*B01L 7/00* (2006.01)
*B01L 3/00* (2006.01)
(Continued)

(52) U.S. Cl.
CPC .............. *B01L 7/52* (2013.01); *B01L 3/5027* (2013.01); *B01L 3/50851* (2013.01); *B01L 3/50853* (2013.01); *B01L 3/502753* (2013.01); *B01L 2200/10* (2013.01); *B01L 2200/16* (2013.01); *B01L 2300/0858* (2013.01); *B01L 2300/0867* (2013.01); *B01L 2300/0883* (2013.01); *B01L 2400/0478* (2013.01); *C12Q 1/6813* (2013.01); *C12Q 1/6844* (2013.01)

(58) Field of Classification Search
CPC ........................................................ B01L 7/52
USPC ........................................................ 422/502
See application file for complete search history.

(56) References Cited

U.S. PATENT DOCUMENTS 5,637,469 A    6/1997    Wilding et al.
2004/0157343 A1    8/2004    Sandell
(Continued)

FOREIGN PATENT DOCUMENTS

CN    101126765 A    2/2008
CN    103323605 A    9/2013
(Continued)

*Primary Examiner* — Christine T Mui
*Assistant Examiner* — Emily R. Berkeley
(74) *Attorney, Agent, or Firm* — IPro, PLLC; Qian Gu

(57) ABSTRACT

Disclosed herein is a multi-functional microfluidics device capable of isolation of nucleic acids, purification of nucleic acids, performance of Polymerase Chain Reactions (PCRs), in situ hybridization of nucleic acids, fluorescent signal detections and the like. The apparatus comprises an integration of a plurality of reagent chambers, a sample input, a reaction chamber, a detection chamber, and a waste chamber; wherein the plurality of reagent chambers is fluidly connected to the reaction chamber, and is configured to store a plurality of reagents; wherein the sample input is fluidly connected to the reaction chamber, and is configured to receive a sample; wherein the waste chamber is fluidly connect to the reaction chamber and is configured to receive a reaction waste from the reaction chamber.

22 Claims, 14 Drawing Sheets

(51) Int. Cl.
*C12Q 1/6813* (2018.01)
*C12Q 1/6844* (2018.01)

(56) References Cited

U.S. PATENT DOCUMENTS

| | | | |
|---|---|---|---|
| 2009/0291505 A1* | 11/2009 | Sarofim | B01L 3/50851 |
| | | | 436/94 |
| 2012/0178091 A1* | 7/2012 | Glezer | B01L 3/5027 |
| | | | 435/6.12 |
| 2014/0146636 A1 | 5/2014 | Dillion | |
| 2015/0093771 A1 | 4/2015 | Griss et al. | |

FOREIGN PATENT DOCUMENTS

| | | | |
|---|---|---|---|
| CN | 105349401 A | 2/2016 | |
| CN | 105195243 B | 10/2017 | |
| WO | 2010141921 A1 | 12/2010 | |
| WO | 2014108087 A1 | 7/2014 | |

* cited by examiner

MULTI-FUNCTIONAL MICROFLUIDICS DEVICE FOR BIOLOGICAL SAMPLE SCREENING

TECHNICAL FIELD

The disclosure herein relates to devices for biological sample screening, particularly multi-functional microfluidics devices capable of isolation of nucleic acids, purification of nucleic acids, performance of Polymerase Chain Reactions (PCRs), in situ hybridization of nucleic acids, fluorescent signal detections and the like.

BACKGROUND

A microfluidics chip or lab-on-a-chip (LOC) is a device that integrates one or several laboratory functions such as in the fields of chemistry, optics, biology and physics on a single chip of only millimeters to a few centimeters to achieve automation and high-throughput screening. Microfluidics technology enables handling and study of extremely small fluid volumes as little as a few pico liters. The technology may be utilized to construct a microscale chemical or biological lab on a chip with an integrated function of isolation, purification of nucleic acids and identification of target molecules from a biological sample.

A microfluidics chip device may be useful in miniaturizing diagnosis assays. For example, a microfluidics chip device may be used for screening biological samples in the fields without sophisticated equipment, or be used by a patient who is not in a clinic or hospital or lives in areas with limited healthcare resources. Microfluidics chip devices may also be utilized in large scale genomic screening projects or genetic testing centers because of the following advantages: low fluid volumes consumption, lower reagents costs, less required sample volumes for diagnostics, faster and simpler analysis and response times due to short diffusion distances, fast heating, better system control because of a faster response of the system, compactness of the systems due to integration of much functionality and small volumes, massive parallelization due to compactness, which allows high-throughput analysis and relatively lower fabrication costs and ability of mass production.

SUMMARY

Disclosed herein is an apparatus comprising: an integration of a plurality of reagent chambers, a sample input, a reaction chamber, a detection chamber, and a waste chamber; wherein the plurality of reagent chambers is fluidly connected to the reaction chamber, and is configured to store a plurality of reagents; wherein the sample input is fluidly connected to the reaction chamber, and is configured to receive a sample; wherein the waste chamber is fluidly connect to the reaction chamber and is configured to receive a reaction waste from the reaction chamber.

According to an embodiment, the apparatus further comprising a mixing channel, wherein the mixing channel is fluidly connected to the plurality of reagent chambers and is configured to mix fluid flowing through the mixing channel.

According to an embodiment, a sidewall of the reaction chamber comprises a protrusion toward an interior of the reaction chamber.

According to an embodiment, the plurality of reagent chambers is configured to couple to one or more actuators, wherein the actuators are configured to actively transfer fluid between the plurality of reagent chambers and the reaction chamber.

According to an embodiment, the one or more actuators comprise a syringe or a micro pump.

According to an embodiment, the detection chamber is configured to couple to an actuator that is configured to actively transfer fluid from the detection chamber to an exterior of the apparatus.

According to an embodiment, the apparatus further comprising an exit chamber; wherein the exit chamber is fluidly connected to the detection chamber; wherein the exit chamber is configured to couple to an actuator that is configured to actively transfer fluid from the detection chamber to the exit chamber.

According to an embodiment, the actuator comprises a syringe or a micro pump.

According to an embodiment, the reaction chamber comprises a first opening at a bottom of the reaction chamber, and the first opening is fluidly connected to the plurality of reagent chambers; wherein the reaction chamber comprises a second opening at the bottom of the reaction chamber, and the second opening is fluidly connected to the detection chamber; wherein the reaction chamber comprises a third opening away from the bottom of the reaction chamber, and the third opening is fluidly connected to the waste chamber.

According to an embodiment, the apparatus, further comprising a capillary passage configured to passively transfer fluid through capillary forces from the sample input to the reaction chamber.

According to an embodiment, the apparatus further comprising one or more channels configured to transfer fluid between the plurality of reagent chambers and the reaction chamber, or to transfer fluid from the reaction chamber to the waste chamber.

According to an embodiment, the apparatus further comprising a channel configured to transfer fluid from the reaction chamber to the detection chamber.

According to an embodiment, the apparatus further comprising a top cover plate, and the top cover plate comprises an opening for receiving the sample.

According to an embodiment, the apparatus further comprising an air vent from the waste chamber to an exterior of the apparatus.

According to an embodiment, the apparatus comprises a material selected from a group consisting of polymethylmethacrylate or polycarbonate.

According to an embodiment, the apparatus is configured to extract and purify nucleic acids from the sample.

According to an embodiment, the apparatus is configured to perform polymerase chain reactions (PCRs).

According to an embodiment, the apparatus is configured to perform nucleic acid in situ hybridization.

According to an embodiment, the detection chamber comprises an array of molecules.

According to an embodiment, the array of molecules comprises a single-stranded nucleic acid sequence that is complementary in sequence to a predetermined nucleic acid molecule of interest.

Disclosed herein is a method of using said apparatus for extracting nucleic acids, comprising: adding a sample to the reaction chamber; adding a lysis buffer from one of the plurality of reagent chambers to the reaction chamber; adding a solution of magnetic beads to the reaction chamber and extracting nucleic acids by association of nucleic acids with the magnetic beads; applying a magnetic field to the reaction chamber to secure the nucleic acids on magnetic beads to a bottom of the reaction chamber; adding a wash buffer to the reaction chamber and washing cellular lysate to the waste chamber; adding an elution buffer to release nucleic acids from the magnetic bead; applying a magnetic field to the reaction chamber to secure the magnetic beads to the bottom of the reaction chamber; obtaining the nucleic acids.

Disclosed herein is a method of using an apparatus described herein for amplifying nucleic acids, comprising: adding a sample to the detection chamber or obtaining a nucleic acid in the detection chamber; adding PCR reagents to the detection chamber; performing PCR by cycling the temperature of the detection chamber; obtaining the amplified nucleic acids.

Disclosed herein is a method of using an apparatus described herein for detecting a nucleic acid of interest, comprising: adding a sample to the detection chamber or obtaining a nucleic acid in the detection chamber; wherein the detection chamber comprises an array of molecules as probes for in situ hybridization reactions; adding a denaturing buffer to the detection chamber; subjecting the detection chamber to a denaturing temperature and dissociating a double-stranded nucleic acid in the sample into a single-stranded nucleic acid; subjecting the detection chamber to an annealing temperature and anneal a single-stranded nucleic acid with a complementary single stranded probe in the array of molecules; adding a wash buffer to the detection chamber; detecting a nucleic acid of interest.

DETAILED DESCRIPTION

Figure 1A:
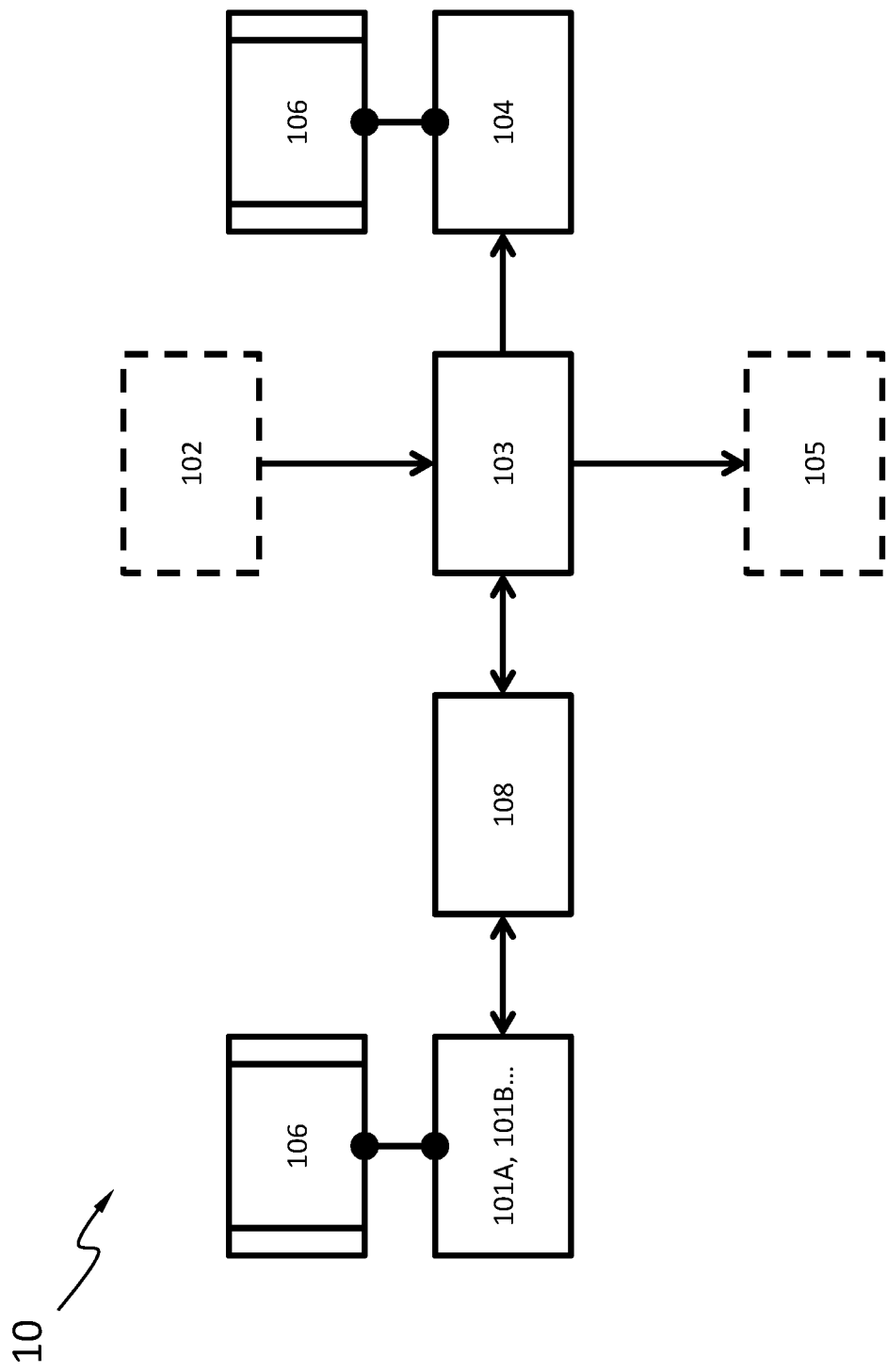
FIG. 1A is a flow chart schematically showing the various components in a multi-functional microfluidics apparatus, according to an embodiment.
Figure 1B:
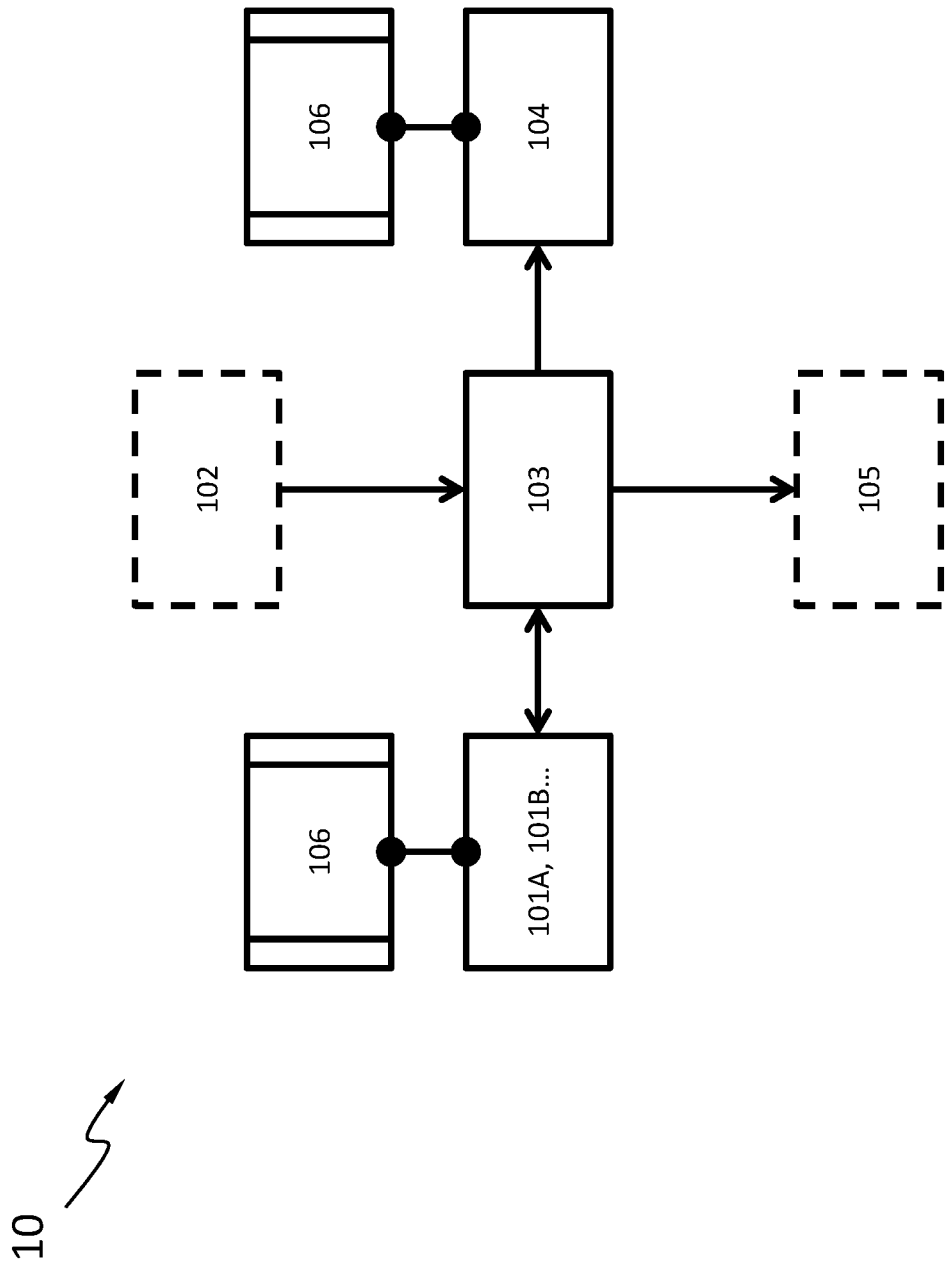
FIG. 1B is a flow chart schematically showing the various components in another multi-functional microfluidics apparatus, according to an embodiment.

The present disclosure provides a multi-functional microfluidics device or apparatus that can extract and purify nucleic acids from biological samples such as blood, saliva, urine, or bacteria cultures etc, and can amplify nucleic acids based on PCRs, fluorescent PCRs, RT-PCRs etc, and can identify the existence of one or more target fragments through in situ hybridizations or other reactions. FIG. 1A-1B schematically shows a multi-functional microfluidics apparatus 10 comprising a plurality of reagent chamber 101A, 101B, a reaction chamber 103, a detection chamber 104, and a waste chamber 105.

Figure 2A:
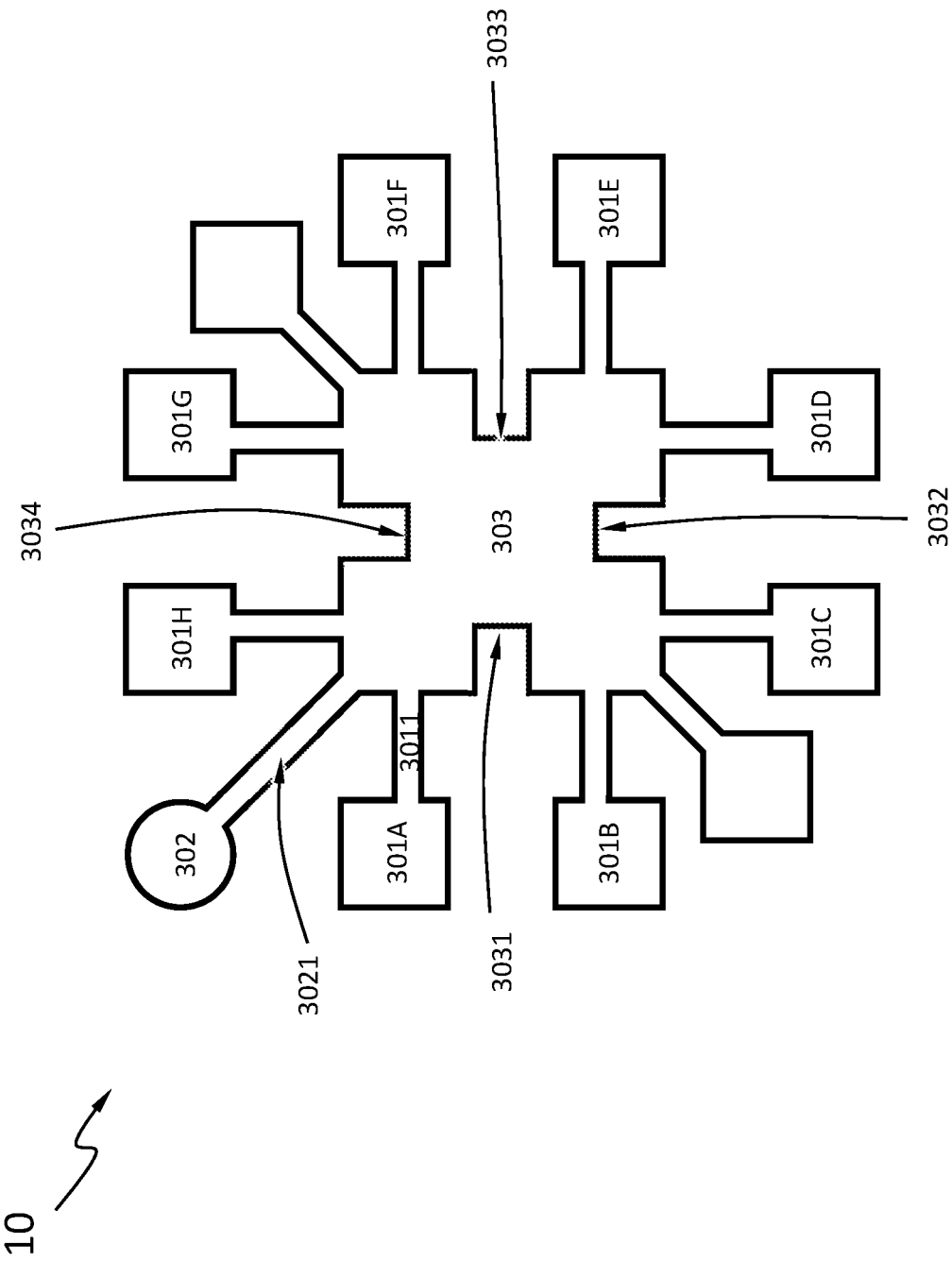
FIG. 2A schematically shows a cross section view of one layout of a multi-functional microfluidics apparatus, according to an embodiment.
Figure 2B:
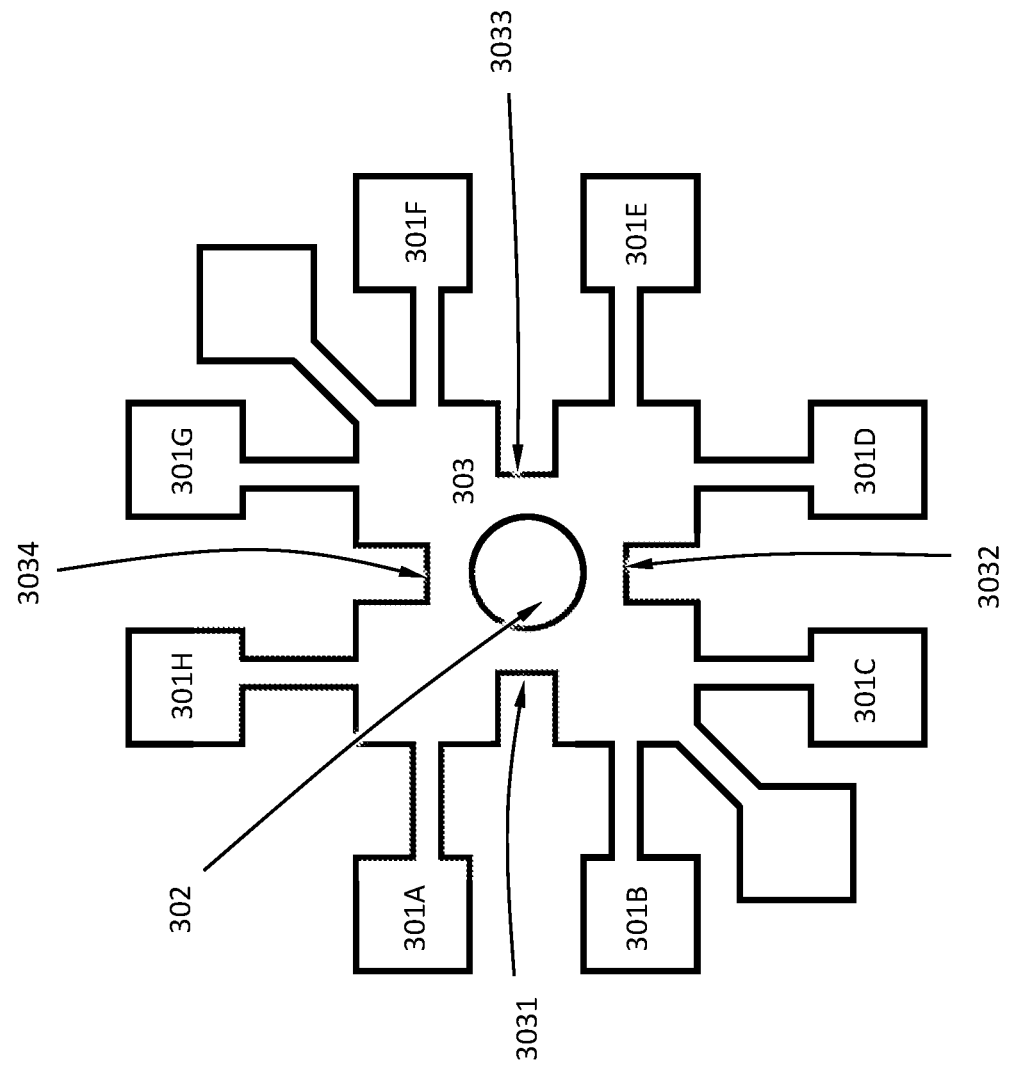
FIG. 2B schematically shows a cross section view of another layout of a multi-functional microfluidics apparatus, according to an embodiment.
Figure 5A:
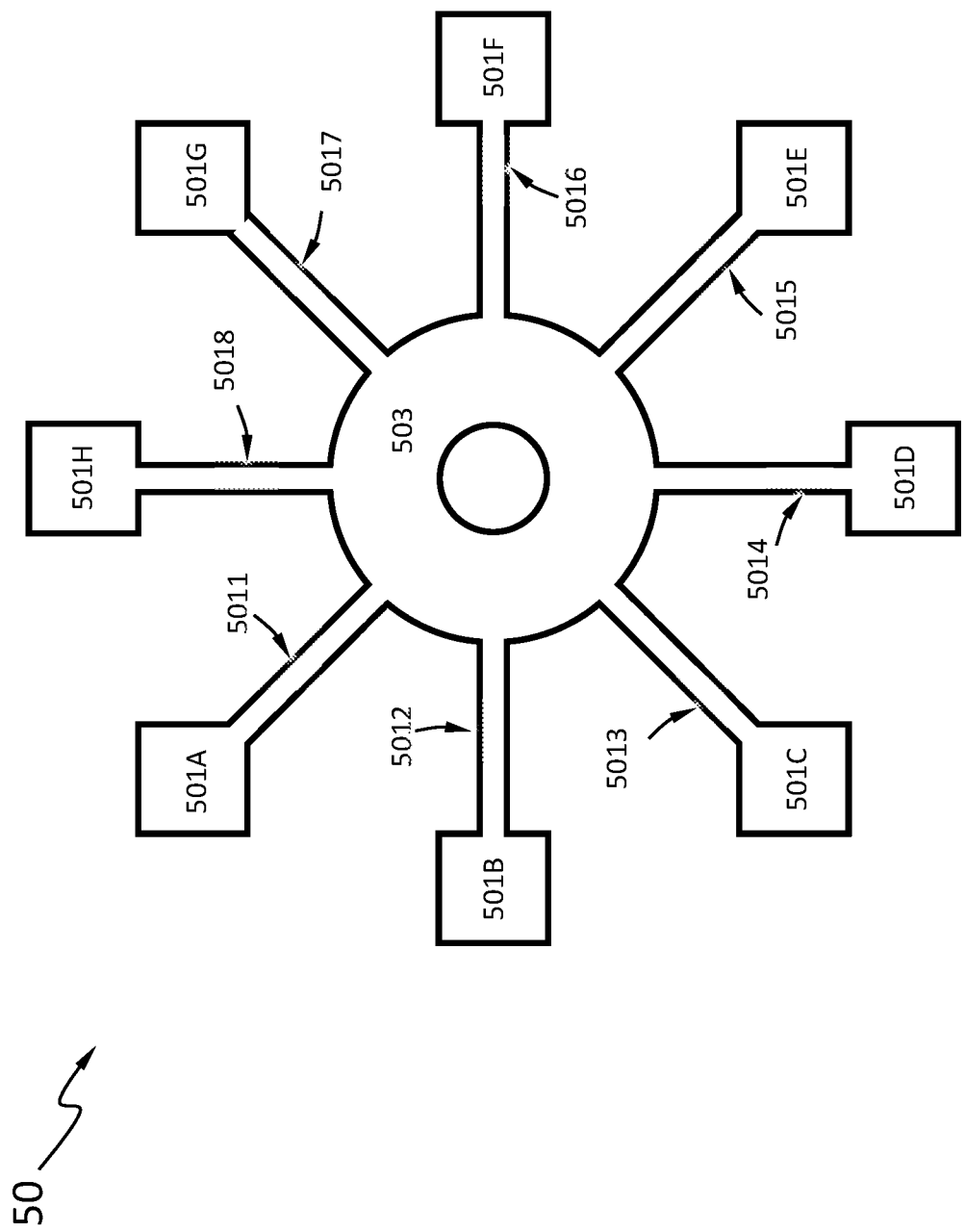
FIG. 5A schematically shows a cross section view of another layout of a multi-functional microfluidics apparatus with an alternative arrangement of the reagent chambers, according to an embodiment.
Figure 5B:
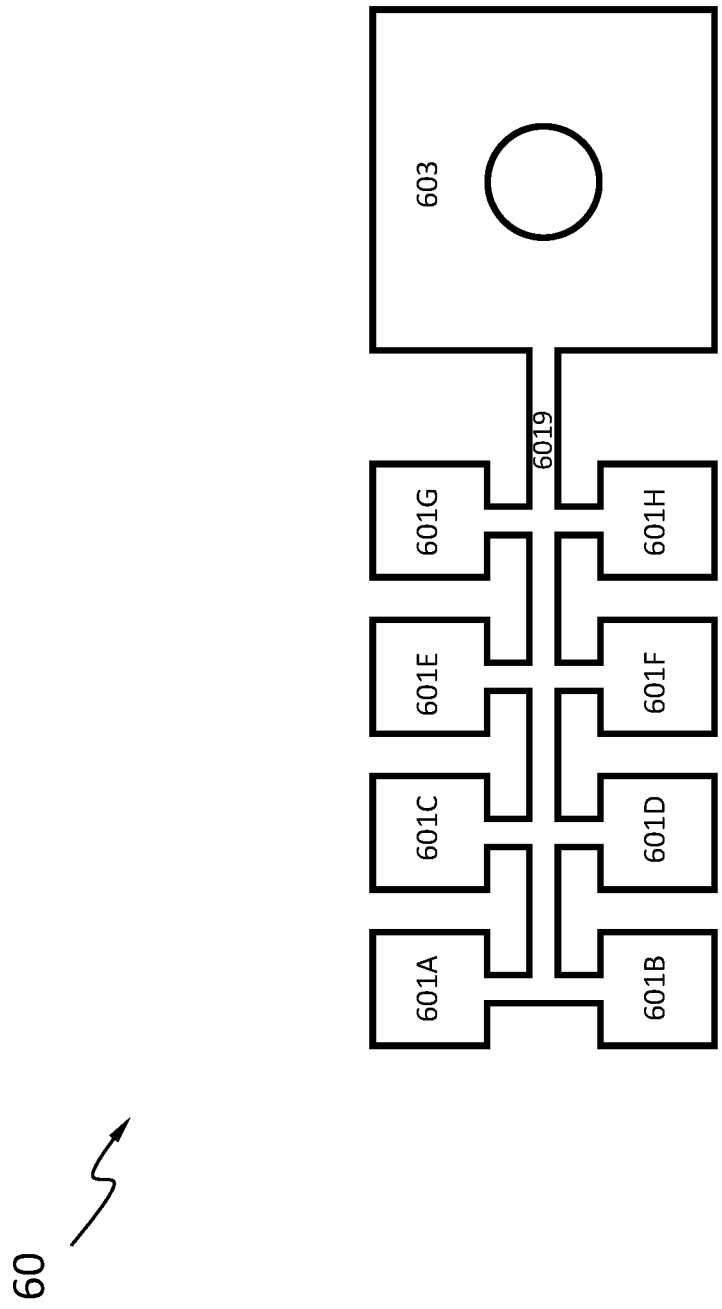
FIG. 5B schematically shows a cross section view of another layout of a multi-functional microfluidics apparatus with an alternative arrangement of the reagent chambers, according to an embodiment.
Figure 6C:
FIG. 6A-6D schematically shows respectively a cross section view of a layout of a mixing channel of a multi-functional microfluidics apparatus, according to various embodiments.
Figure 6D:
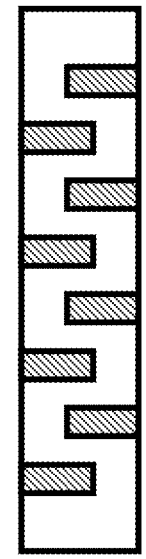
Figure 6A:
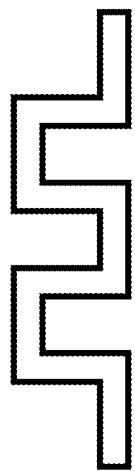
Figure 6B:
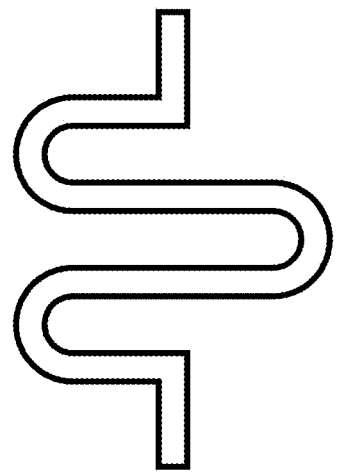

The reagent chambers are fluidly connected to the reaction chamber and may store reagents used for nucleic acids isolation, purification and identification. As shown in FIG. 2A-2B, eight reagent chambers 301A, 301B, 301C, 301D, 301E, 301F, 301G, 301H are each fluidly connected to the reaction chamber through a channel. The number of reagent chambers is often predetermined based on the type of reaction or screening to be performed. Various arrangements of the reagent chambers may be provided. In one example, each of the reagent chambers 501A, 501B, 501C, 501D, 501E, 501F, 501G, 501H may employ its unique channel 5011, 5012, 5013, 5014, 5015, 5016, 5017, 5018 respectively to access the reaction chamber 503, as shown in apparatus 50 according to an embodiment in FIG. 5A. Alternative, each of the reagent chambers 601A, 601B, 601C, 601D, 601E, 601F, 601G, 601H may share a segment of a common channel 6019 to access the reaction chamber 603, as shown in apparatus 60 according to an embodiment in FIG. 5B. Other components in the apparatus are not shown in FIG. 5.

As shown in FIG. 1, the apparatus 10 may receive a sample from a sample input 102. The sample input may a storage space for receiving a biological sample such as a blood or saliva sample. As shown in FIG. 2A, the sample input 302 is fluidly connected to the reaction chamber 303 through a sample passage 3021, which passively transfers sample through capillary forces from the sample input 302 to the reaction chamber 303. Alternatively, as shown in FIG. 2B, the sample input may be an opening 302 on the reaction chamber 303. Other designs may be suitable as well. For example, as shown in FIG. 3, FIG. 4A, FIG. 4B and FIG. 4C, the apparatus 40 comprise a top cover plate 41, a middle level 42 and a bottom plate 43. During use, a sample may be added through an opening 411 on the top cover plate 41 into the sample input 402 in the middle level 42. Alternatively, in another embodiment, a sample may be added into a reaction chamber directly through an opening on a top cover plate that is positioned to be on top of the reaction chamber.

As shown in FIG. 1, the apparatus 10 may also have a mixing channel 108 that fluidly connects the plurality of reagent chambers 101 to the reaction chamber 103. Mixing channels may have various shapes and designs that are suitable for fluid mixing. When in use, a user may enable additional mixing by using the actuator 106 coupled to the reagent chamber to push a reagent through the mixing channel 108 into the reaction chamber 103, draw the reagent back into the reagent chamber and repeat a few more times. Actuators may achieve active fluid transfer within the apparatus through channels between different chambers, which is in contrast to the passive fluid transfer through capillary forces. As shown in FIG. 6A-6D, according to various embodiments, mixing channels may be a channel with a plurality of turns of 90 degree angle, a U-shaped channel, a zig-zag shaped channel, or a straight elongated channel with a plurality of interior-protruding plates on its interior walls. Alternatively, mixing channels may be omitted in an apparatus as shown in FIG. 1B, and a user may still provide mixing of reagents and sample by using actuators coupled to the reagent chamber. Such an actuator may be a syringe or a micro pump.

In other embodiments as shown in 2A-2B, mixing function may be realized by structures on the reaction chamber 303. For example, as shown in an embodiment in FIG. 2A, the sidewall of the reaction chamber comprises protrusions 3031, 3032, 3033 and 3034 toward an interior of the reaction chamber. Protrusions 3031, 3032, 3033 and 3034 comprise a plurality of turns of 90 degree angle. Other types of protrusions on the sidewall of the reaction chamber may also designed for realizing the fluid mixing function.

Figure 3:
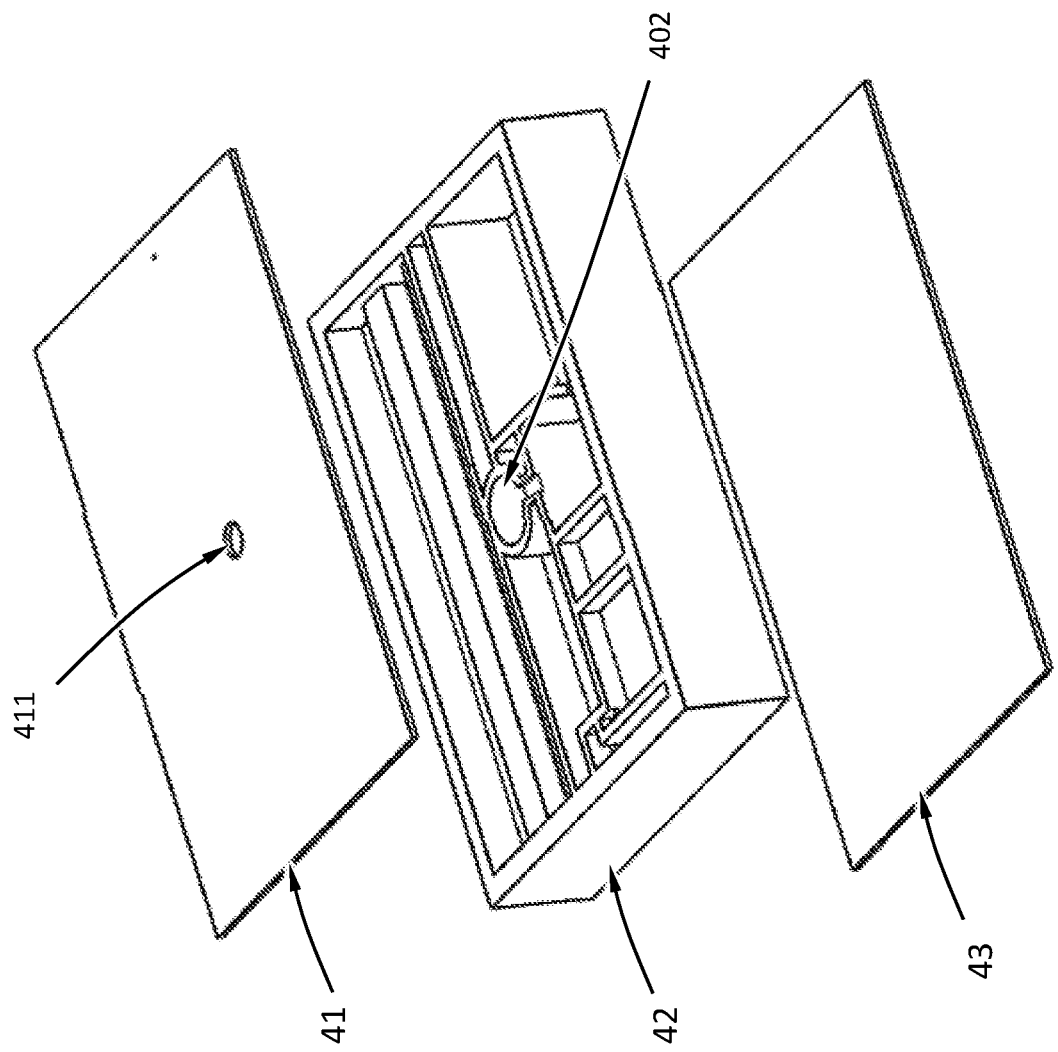
FIG. 3 schematically shows an explosion view of a multi-functional microfluidics apparatus with a multi-layer structure, according to an embodiment.

As shown in FIG. 3, in one embodiment, the top cover plate 41 and the bottom plate 43 may be made of a suitable material including but not limited to glass. The middle level 42 may be made of a suitable material, including but not limited to glass, or polymers such as polymethylmethacrylate or polycarbonate. In one example, when PCR reactions are to be performed on the apparatus, the detection chamber comprises a material with a thermal conductivity suitable for performing PCRs. When fluorescent signal detections are to be performed, the detection chamber comprises a material that allows light transmittance in the range of wavelengths from 200 nanometer to 900 nanometer.

Figure 4A:
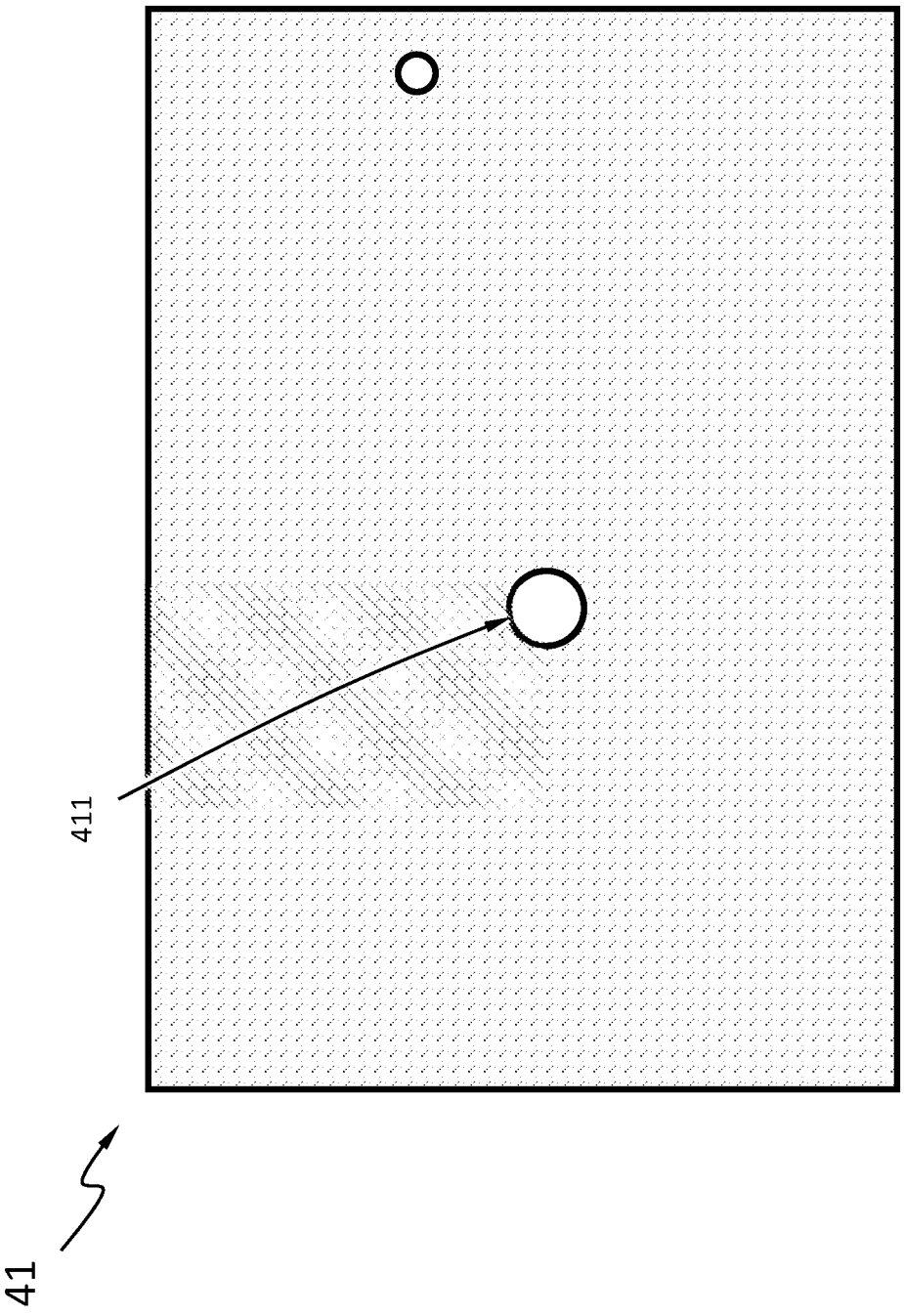
FIG. 4A schematically shows a top view of a top cover of a multi-functional microfluidics apparatus, according to the embodiment in FIG. 3.
Figure 4B:
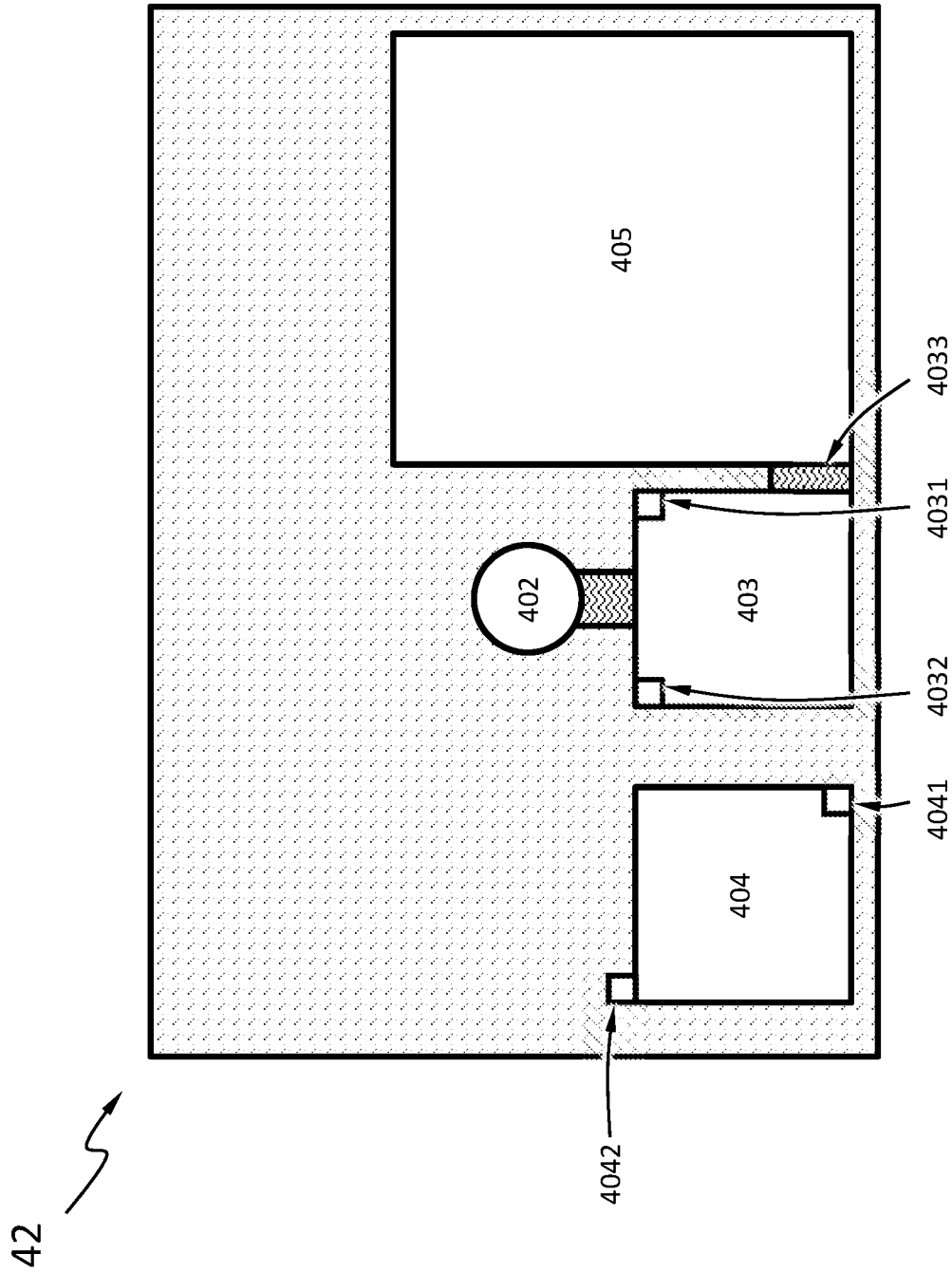
FIG. 4B schematically shows a top view of a first layer of a multi-functional microfluidics apparatus, according to the embodiment in FIG. 3.
Figure 4C:
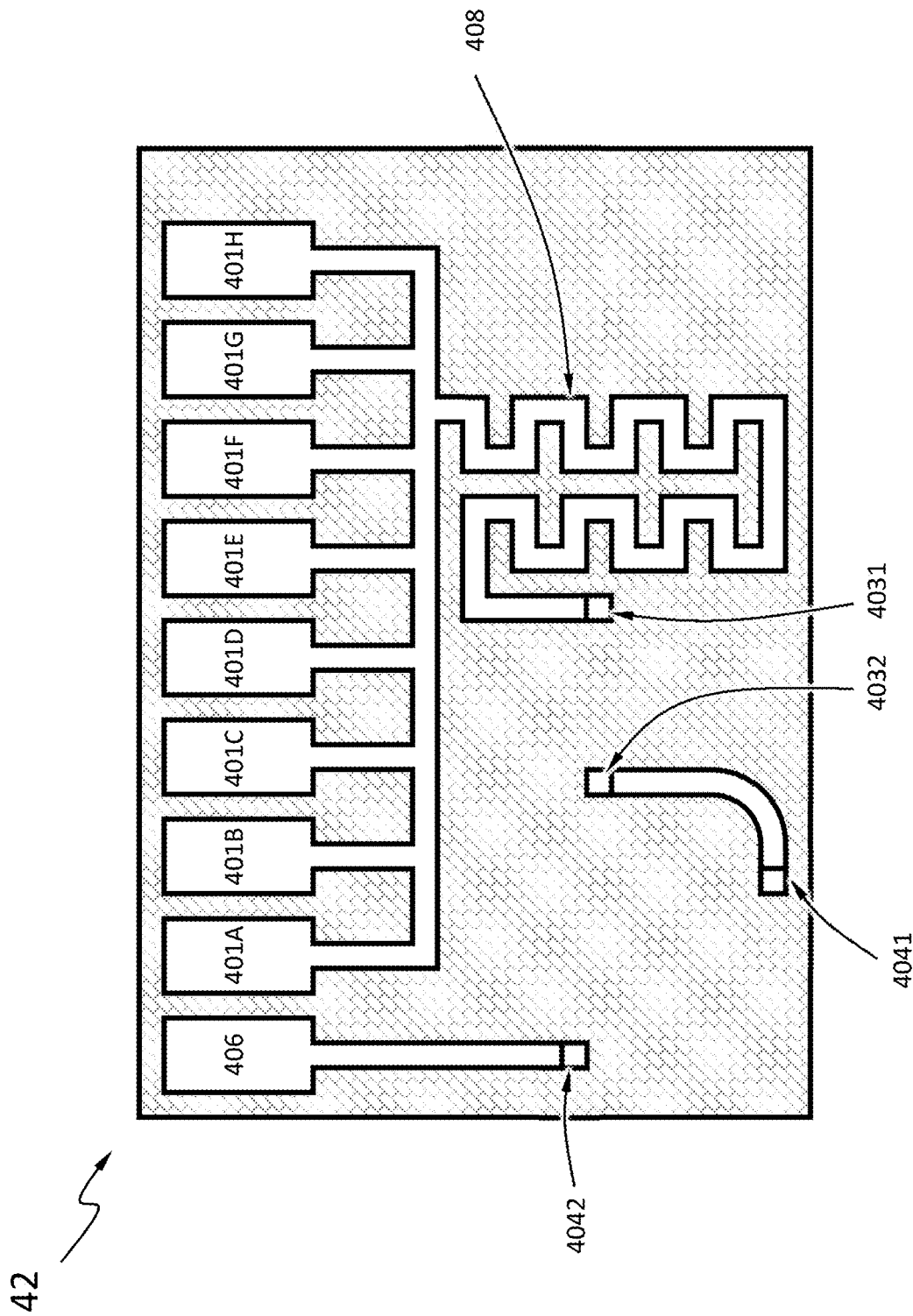
FIG. 4C schematically shows a top view of a second layer of a multi-functional microfluidics apparatus, according to the embodiment in FIG. 3.
Figure 4D:
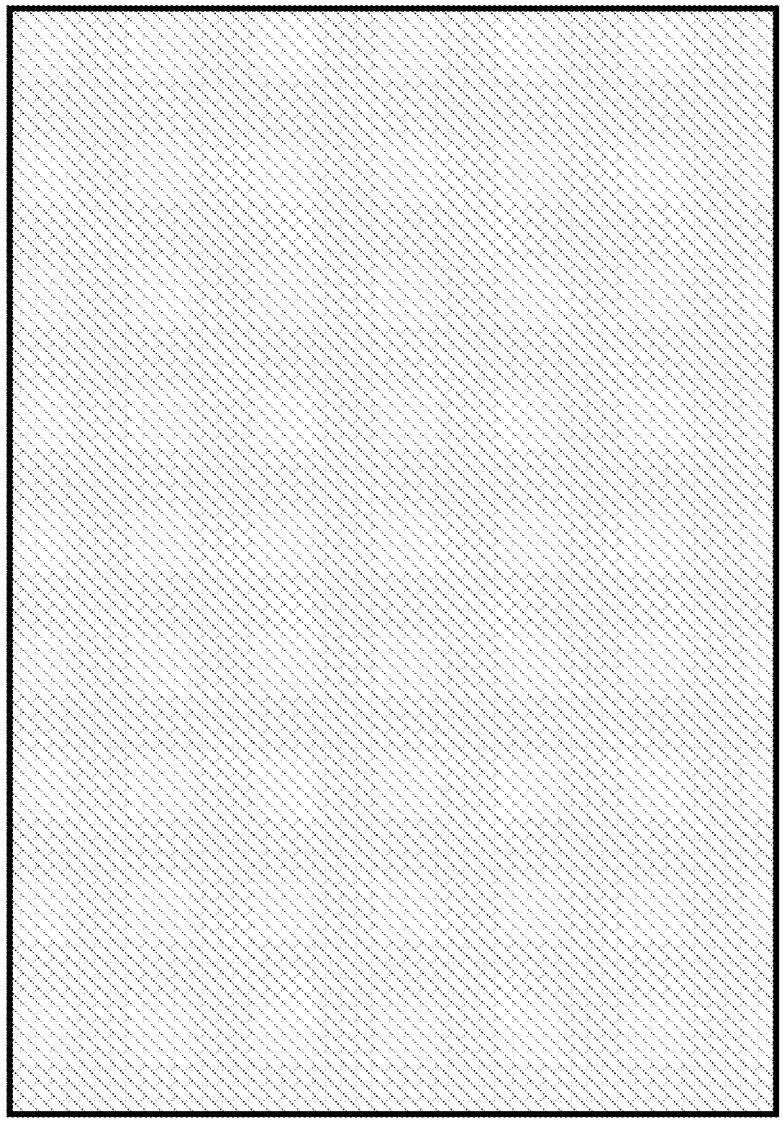
FIG. 4D schematically shows a top view of a bottom plate of a multi-functional microfluidics apparatus, according to the embodiment in FIG. 3.

As shown in FIG. 4B-4C, in one embodiment, the reaction chamber 403 comprises a first opening 4031 at a bottom of the reaction chamber 403, and the first opening 4031 is fluidly connected to the plurality of reagent chambers 401A-401H through a mixing channel 408. The reaction chamber 403 comprises a second opening 4032 at a bottom of the reaction chamber, and the second opening is fluidly connected to the detection chamber 404. Furthermore, the reaction chamber 403 comprises a third opening 4033 away from the bottom of the reaction chamber, and the third opening 4033 is fluidly connected to the waste chamber 405. In one example, the third opening 4033 may be at a top of the reaction 403.

As shown in FIG. 4B-4C, the detection chamber 404 may comprise a first opening 4041 at a bottom of the detection chamber 404, and the first opening 4041 is fluidly connected to the reaction chambers 403. The detection chamber 404 may comprise a second opening 4042 at a bottom of the detection chamber 404, and the second opening 4042 is fluidly connected to the exit chambers 406.

For achieving a compact design, various layouts including but not limited to multiple layered apparatus may be provided. In one example as shown in FIG. 4B-4C, the waste chamber 405 may be partially stacked on top of the mixing channels 408. Stacking of component chambers may save space and reduce manufacturing cost.

Figure 7B:
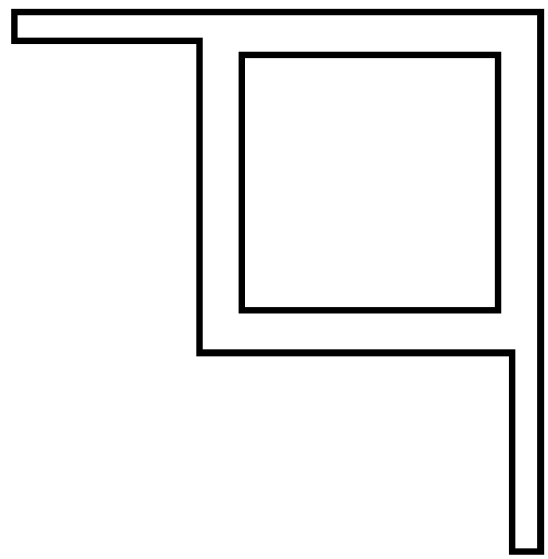
FIG. 7A-7B schematically shows respectively a cross section view of a layout of a detection chamber of a multi-functional microfluidics apparatus, according to various embodiments.
Figure 7A:
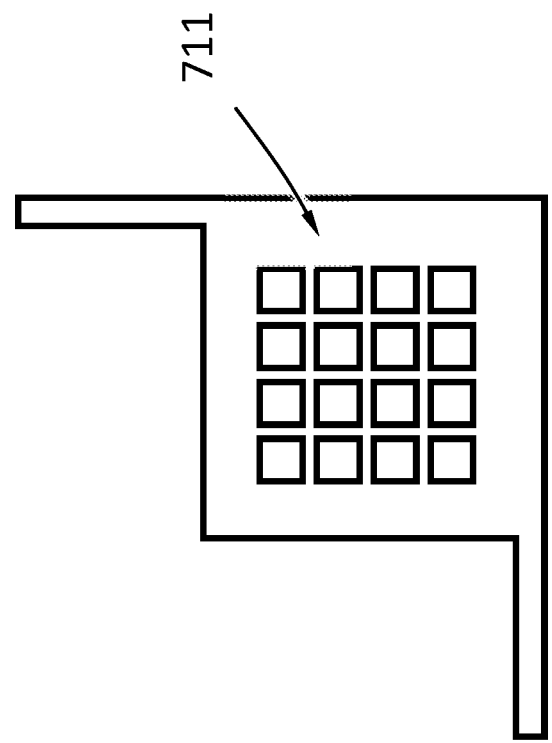

A variety of detection assays may be designed to be performed with the apparatus. For example, apparatus may be configured to perform nucleic acid in situ hybridization; and as such the detection chamber may have an array of molecules precoated on one or more slides 711 annexed to the detection chamber, as shown in FIG. 7A. Alternatively, apparatus may be configured to perform polymerase chain reactions (PCRs), and the detection chamber may be a single chamber as shown in FIG. 7B.

Various operations or reactions may be performed with the apparatus. Embodiments of methods of using the apparatus disclosed below are for purpose of illustration and are not intended to be limiting. It is conceivable that variations of the structures of the apparatus may be implemented to carry out the same or similar operations or reaction.

Disclosed herein is a first embodiment of using the apparatus to extract and purify genomic DNAs from a blood sample.

Figure 8:
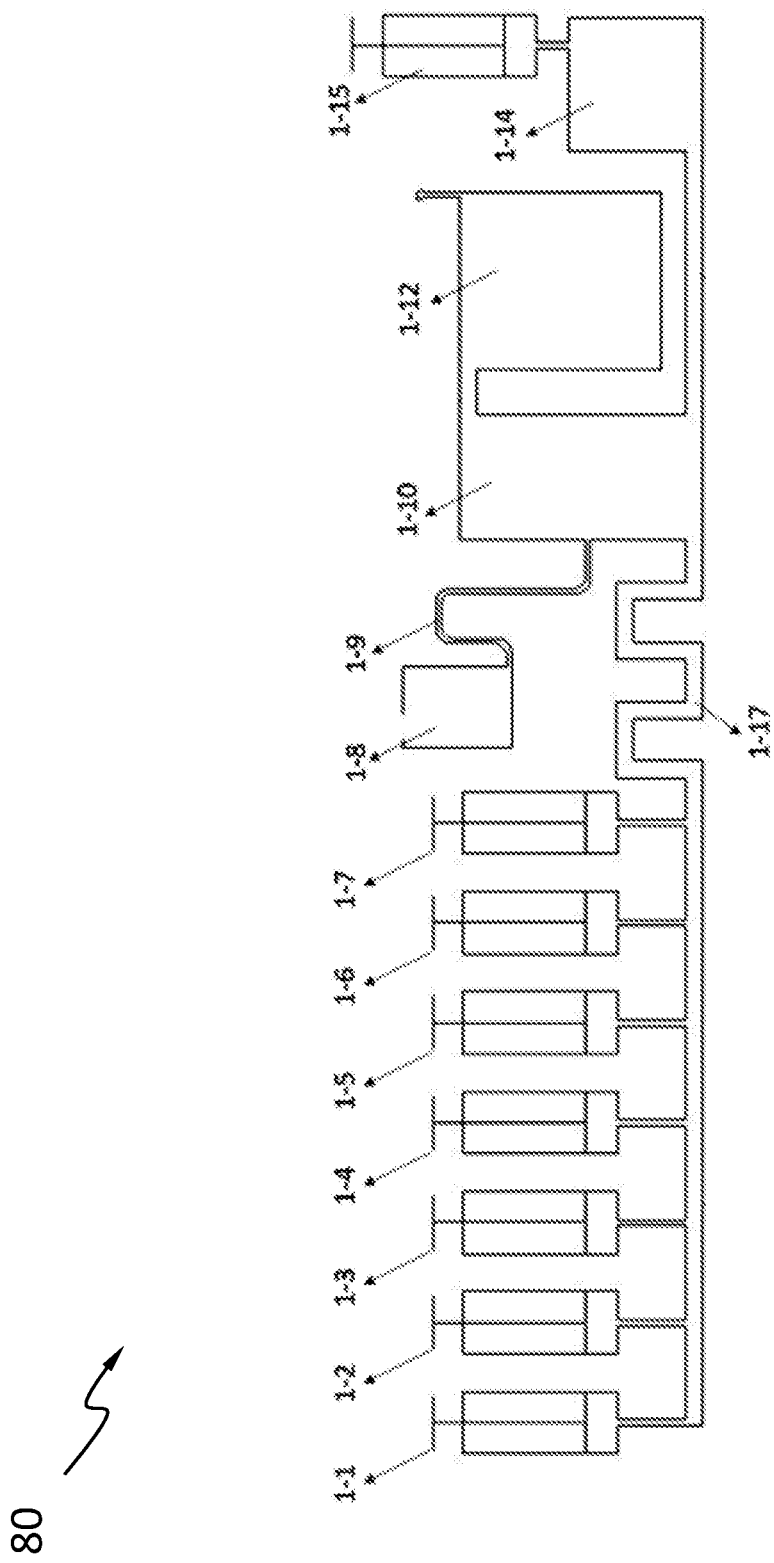
FIG. 8 schematically shows a layout of a multi-functional microfluidics apparatus, according to an embodiment.

Before its use, the apparatus may be prefilled with a plurality of reagents required for the application. In this embodiment, the plurality of reagent chambers may be prefilled with a GeneCatcher gDNA Blood Kit from Thermo Fisher Scientific Inc. for genomics DNA extractions. In theory, any genomics DNA extraction kit suitable for blood sample may be used as well. As an example, as shown in FIG. 8, a reagent chamber 1-1 is prefilled with 2.5 ml lysis buffer L13; a reagent chamber 1-2 is prefilled with 100 µL magnetic beads; a reagent chamber 1-3 is prefilled with 0.5 mL protease buffer; a reagent chamber 1-4 is prefilled with 20 µL protease; a reagent chamber 1-5 is prefilled with 1 mL 100% isopropyl alcohol (IPA); a reagent chamber 1-6 is prefilled with 150 µL wash buffer; and a reagent chamber 1-7 is prefilled with 250 µL elution buffer.

During the use of the apparatus 80, first, add 0.3-1 mL blood sample to the sample input 1-8. Sample is transferred through capillary passage 1-9 from the sample input to the reaction chamber 1-10. Use an actuator such as a syringe coupled to the reagent chamber 1-1 to inject the lysis buffer in the reagent chamber 1-1 into the reaction chamber 1-10 through a mixing channel 1-17, and the lysis buffer is mixed with the sample. Because the detection chamber 1-14 and the exit chamber 1-15 are in a closed mode, the mixture of reagent and sample does not enter into the detection chamber. As used herein, the closed mode may be either a result of a use of valves within a channel, or be achieved through the air pressure in a closed chamber such as detection chamber 1-15. Extra air that is moved by the pressure may enter into the waste chamber and go through an air vent on the waste chamber 1-12 to the exterior of the apparatus.

Next to bind DNA, use a syringe coupled to the reagent chamber 1-2 to transfer a solution of magnetic beads prefilled in the reagent chamber 1-2 to the reaction chamber 1-10 to obtain a magnetic bead-sample-lysis buffer mixture. To mix well, the user may draw the syringe back and forth a couples of times so that the mixture moves between the reaction chamber 1-10 and the reagent chamber 1-2. After mixing and a short period of incubation, applying a magnetic field to secure the magnetic beads associated with genomics DNAs to a bottom of the reaction chamber 1-10. Applying a magnetic field may be done by using an appropriate magnet. Next, to purify DNA, use a syringe coupled to the reagent chamber 1-3 to transfer the protease buffer from the reagent chamber 1-3 to the reaction chamber 1-10. With proper control of the volume of the protease buffer added and the design of suitable size of the waste chamber, essentially all (at least 90%) contents of the supernant containing cellular lysate may be pushed out into the waste chamber 1-12 by the injection of the protease buffer. Next, using a syringe coupled to the reagent chamber 1-4 to transfer the protease from the reagent chamber 1-4 to the reaction chamber 1-10. Remove the magnetic field so that the magnetic beads may become suspended in the protease buffer. Use the syringe coupled to the reagent chamber 1-4 to mix well the content. Adjust the temperature of the reaction chamber by for example placing the apparatus to a heated incubator of suitable temperature such as 65° C. and continue to incubate for a suitable amount of time such as 10 minutes. Nucleic acid may be released from its bounded proteins through the enzyme digestion of the protease. After incubation, apply the magnetic field to secure the magnetic beads associated with genomics DNAs to the bottom of the reaction chamber. Continue DNA purification by using a syringe coupled to the reagent chamber 1-5 to transfer the IPA in the reagent chamber 1-5 to the reaction chamber, which at the same time displacing all contents to the waste chamber. Transfer wash buffer from the reagent chamber 1-6 to the reaction chamber. Remove the magnetic field, and transfer an elution buffer from the reagent chamber 1-7 to the reaction chamber 1-10. Adjust the temperature of the apparatus to 65° C. and continue to incubate for a suitable amount of time such that the purified DNAs are eluted from the magnetic beads. Apply the magnetic field, and obtain the purified DNA by drawing back the syringe coupled to the exit chamber 1-15 and moving the genomic DNAs to the exit chamber. The purified genomic DNAs may be used for any subsequent reactions such as enzyme digestions, PCRs, qPCRs, etc.

Disclosed herein is a second embodiment of using the apparatus to amplify genomic DNAs from a blood sample by PCRs.

The apparatus may be envisioned to have multiple working modes for PCR amplification reactions on the apparatus. A first working mode is to provide an apparatus with prefilled PCR reagents in the reagent chambers. The template DNA, i.e., the DNA to be amplified, may be either prefilled in one of the reagent chambers, or be added through a sample input. Prior to the start of the PCR, sequentially transfer as needed PCR reagents from the reagent chambers to the reaction chamber and mix well. Add the template DNA and mix well. Draw back a syringe coupled to the exit chamber and move the mixture of template DNA and reagents to the detection chamber, which is made of a material with a thermal conductivity suitable for performing polymerase chain reactions (PCRs). Place the apparatus to a PCR cycler device that have temperature control module to perform the required PCR reactions by cycling the temperature of the reaction chamber. After the completion of the PCRs, amplified DNAs may be extracted from the apparatus.

Alternatively, in a second working mode, the template DNA is itself purified through a process described by using the apparatus in combination with a purification kit as described above. The apparatus is prefilled not only with DNA purification reagents but also prefilled with PCR reagents in the reagent chambers. After obtaining purified genomic DNAs and moving it to detection chamber, sequentially transfer as needed PCR reagents from the reagent chambers to the reaction chamber and mix well. Draw back the syringe coupled to the exit chamber and further move the mixture of PCR reagents to the detection chamber. PCRs may be performed on the detection chamber of the apparatus as described above.

As further alteration, the apparatus does not need to have prefilled PCR reagents. For example, a third working mode is to add external PCR reagents and template DNA into an apparatus. PCR reagents and DNA template may be premixed in a tube according to PCR reaction instruction under regular laboratories conditions to obtain a master mixture. Then an appropriate amount of the master mixture may be added to the apparatus through a sample input, and be drawn into the reaction chamber through passive transfer by capillary forces. The master mixture may be moved further to the detection chamber by the drawing back of a syringe coupled to the exit chamber. PCRs may be performed on the detection chamber of the apparatus as described above.

As another example, a fourth working mode is to provide external PCR reagents to existing purified DNA in the reaction chamber. PCR reagents without DNA template may be premixed in a tube according to PCR reaction instruction under regular laboratories conditions to obtain a master PCR reagent mixture. After obtaining purified genomic DNAs using for example the magnetic bead extraction kit as described, an appropriate amount of the master PCR reagent mixture may be added to the apparatus through a sample input, and be drawn into the reaction chamber through passive transfer by capillary forces. Then mix and transfer the purified genomic DNAs and master PCR reagent mixture to the detection chamber by using the syringe coupled to the exit chamber. PCRs may be performed on the detection chamber of the apparatus as described above.

Disclosed herein is a third embodiment of using the apparatus to identify a target DNA fragment from a blood sample by in situ hybridization.

The apparatus may comprise a detection chamber an array of molecules as probes for in situ hybridization reactions or fluorescent signal detections. Probes may comprise a library of small DNA fragments that may be suitable for hybridizing to genomics DNA of interest. Probes may be precoated on a matrix in the detection chamber. Probes may be preselected according to a predetermined testing or screening purpose of the apparatus. A sample of purified genomic DNA may be labelled by fluorescent groups under normal laboratory conditions for fluorescent signal detections. To detect a target of interest within the sample of purified genomic DNA, the sample may be added to the apparatus through sample input, and be drawn into a detection chamber with precoated molecular probes. The apparatus may comprise a plurality of prefilled reagents in reagent chamber suitable for in situ hybridization reactions. The apparatus may be subject to in situ hybridization by transferring hybridization buffers and mixing it with the genomic DNA in the detection chamber. Then subject the detection chamber to a denaturing temperature of for example 92° C. on a temperature controller such that the double strands of genomic DNA become single strands. Subject the detection chamber to an annealing temperature of for example 60° C. such that the target DNA of interest may anneal with a designed DNA probe with sequence complementarity. Transfer wash buffer from a reagent chamber to the detection chamber to wash away unbounded genomic DNAs. Then the bounded target DNA of interest may be detected by fluorescent signal detections.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. An apparatus, comprising:
   an integration of a plurality of reagent chambers, a sample input, a reaction chamber, a detection chamber, and a waste chamber;

wherein the plurality of reagent chambers is fluidly connected to the reaction chamber, and is configured to store a plurality of reagents;

wherein the sample input is fluidly connected to the reaction chamber, and is configured to receive a sample;

wherein the waste chamber is fluidly connected to the reaction chamber and is configured to receive a reaction waste from the reaction chamber;

wherein a sidewall of the reaction chamber comprises a protrusion toward an interior of the reaction chamber such that the reaction chamber has a non-uniform cross-sectional area;

wherein the reaction chamber comprises a first opening at a bottom of the reaction chamber, and the first opening is fluidly connected to the plurality of reagent chambers;

wherein the reaction chamber comprises a second opening at the bottom of the reaction chamber, and the second opening is fluidly connected to the detection chamber; and wherein the reaction chamber comprises a third opening away from the bottom of the reaction chamber, the third opening is fluidly connected to the waste chamber, and the third opening does not extend an entire height of the reaction chamber.

2. The apparatus of claim 1, further comprising a mixing channel,
wherein the mixing channel is fluidly connected to the plurality of reagent chambers and is configured to mix fluid flowing through the mixing channel.

3. The apparatus of claim 1, wherein the plurality of reagent chambers is configured to couple to one or more actuators, wherein the actuators are configured to actively transfer fluid between the plurality of reagent chambers and the reaction chamber.

4. The apparatus of claim 3, wherein the one or more actuators comprise a syringe or a micro pump.

5. The apparatus of claim 1, wherein the detection chamber is configured to couple to an actuator that is configured to actively transfer fluid from the detection chamber to an exterior of the apparatus.

6. The apparatus of claim 1, further comprising an exit chamber; wherein the exit chamber is fluidly connected to the detection chamber; wherein the exit chamber is configured to couple to an actuator that is configured to actively transfer fluid from the detection chamber to the exit chamber.

7. The apparatus of claim 6, wherein the actuator comprises a syringe or a micro pump.

8. The apparatus of claim 1, further comprising a capillary passage configured to passively transfer fluid through capillary forces from the sample input to the reaction chamber.

9. The apparatus of claim 1, further comprising one or more channels configured to transfer fluid between the plurality of reagent chambers and the reaction chamber, or to transfer fluid from the reaction chamber to the waste chamber.

10. The apparatus of claim 1, further comprising a channel configured to transfer fluid from the reaction chamber to the detection chamber.

11. The apparatus of claim 1, further comprising a top cover plate, and the top cover plate comprises an opening for receiving the sample.

12. The apparatus of claim 1, further comprising an air vent from the waste chamber to an exterior of the apparatus.

13. The apparatus of claim 1, wherein the apparatus comprises a material selected from a group consisting of polymethylmethacrylate or polycarbonate.

14. The apparatus of claim 1, wherein the apparatus is configured to extract and purify nucleic acids from the sample.

15. The apparatus of claim 1, wherein the apparatus is configured to perform polymerase chain reactions (PCRs).

16. The apparatus of claim 1, wherein the apparatus is configured to perform nucleic acid in situ hybridization.

17. The apparatus of claim 1, wherein the detection chamber comprises an array of molecules.

18. The apparatus of claim 17, wherein the array of molecules comprises a single-stranded nucleic acid sequence that is complementary in sequence to a predetermined nucleic acid molecule of interest.

19. A method of using an apparatus of claim 1 for extracting nucleic acids, comprising:
adding a sample to the reaction chamber;
adding a lysis buffer from one of the plurality of reagent chambers to the reaction chamber;
adding a solution of magnetic beads to the reaction chamber and extracting nucleic acids by association of nucleic acids with the magnetic beads;
applying a magnetic field to the reaction chamber to secure the nucleic acids on magnetic beads to a bottom of the reaction chamber;
adding a wash buffer to the reaction chamber and washing cellular lysate to the waste chamber;
adding an elution buffer to release nucleic acids from the magnetic bead;
applying a magnetic field to the reaction chamber to secure the magnetic beads to the bottom of the reaction chamber;
obtaining the nucleic acids.

20. A method of using an apparatus of claim 1 for amplifying nucleic acids, comprising:
adding a sample to the detection chamber or obtaining a nucleic acid in the detection chamber;
adding PCR reagents to the detection chamber;
performing PCR by cycling a temperature of the detection chamber;
obtaining the amplified nucleic acids.

21. A method of using an apparatus of claim 1 for detecting a nucleic acid of interest, comprising:
adding a sample to the detection chamber or obtaining a nucleic acid in the detection chamber; wherein the detection chamber comprises an array of molecules as probes for in situ hybridization reactions;
adding a denaturing buffer to the detection chamber;
subjecting the detection chamber to a denaturing temperature and dissociating a double-stranded nucleic acid in the sample into a single-stranded nucleic acid;
subjecting the detection chamber to an annealing temperature and anneal a single-stranded nucleic acid with a complementary single stranded probe in the array of molecules;
adding a wash buffer to the detection chamber;
detecting a nucleic acid of interest.

22. The apparatus of claim 1, wherein the protrusion is configured to mix fluid in the reaction chamber.

* * * * *